United States Patent
Weijand et al.

[11] Patent Number: 6,009,878
[45] Date of Patent: Jan. 4, 2000

[54] SYSTEM FOR LOCATING IMPLANTABLE MEDICAL DEVICE

[75] Inventors: Koen J. Weijand, Rockanje, Netherlands; Markus Haller, Begnins, Switzerland

[73] Assignee: Medtronic, Inc., Minneapolis, Minn.

[21] Appl. No.: 09/017,198

[22] Filed: Feb. 2, 1998

[51] Int. Cl.⁷ .................................................. A61B 19/00
[52] U.S. Cl. ........................................ 128/899; 600/424
[58] Field of Search ..................... 600/424; 128/897–899

[56] References Cited

U.S. PATENT DOCUMENTS

| | | |
|---|---|---|
| 4,441,498 | 4/1984 | Nordling . |
| 4,542,532 | 9/1985 | McQuilkin ................................ 455/78 |
| 4,757,816 | 7/1988 | Ryan et al. . |
| 4,760,837 | 8/1988 | Petit . |
| 5,006,115 | 4/1991 | McDonald ............................... 604/175 |
| 5,009,644 | 4/1991 | McDonald ............................... 604/175 |
| 5,171,228 | 12/1992 | McDonald ............................... 604/175 |
| 5,325,873 | 7/1994 | Hirschi et al. ....................... 600/424 X |
| 5,425,367 | 6/1995 | Shapiro .................................... 600/424 |
| 5,513,637 | 5/1996 | Twiss et al. ............................. 600/424 |
| 5,622,169 | 4/1997 | Golden et al. ........................... 600/424 |
| 5,727,552 | 3/1998 | Ryan .................................... 128/899 X |

*Primary Examiner*—Samuel Gilbert
*Attorney, Agent, or Firm*—Thomas F. Woods; Harold Patton; Michael J. Jaro

[57] ABSTRACT

A system and method for locating an implantable medical device. The system consists of a flat "pancake" antenna coil positioned concentric with the implantable medical device target, e.g. the drug reservoir septum. The system further features a three location antenna array which is separate from the implantable device and external to the patient. The antenna array features three or more separate antennas which are used to sense the energy emitted from the implanted antenna coil. The system further features a processor to process the energy ducted by the antenna array. The system senses the proximity to the implant coil and, thus, the implant device by determining when an equal amount of energy is present in each of the antennas of the antenna array and if each such ducted energy is greater than a predetermined minimum. When such a condition is met, the antenna array is aligned with the implant coil. Thus the needle port through the antenna array is lined up with the septum of the drug reservoir. Alternative embodiments are further disclosed in which the processor and antenna array are positioned within the implanted device while the coil is external to the patient.

3 Claims, 6 Drawing Sheets

//6,009,878//

SYSTEM FOR LOCATING IMPLANTABLE MEDICAL DEVICE

RELATED APPLICATIONS

This application is related to one or more of the following each of which are filed on this same day each incorporated herein by reference and each assigned to the assignee of the present application:

U.S. patent application Ser. No. 09/017,194 filed Feb. 2, 1998 entitled "Implantable Drug Infusion Device Having A Flow Regulator" of Markus Haller, Phillipe Renaud and Christian Amacker U.S. patent application Ser. No. 09/017,195 filed Feb. 2, 1998 entitled "Implantable Drug Infusion Device Having A Safety Valve" of Markus Haller and Koen Weijand; and U.S. patent application Ser. No. 09/017,196 filed Feb. 2, 1998 entitled "Implantable Drug Infusion Device Having An Improved Valve" of Markus Haller, T. S. J. Lammerink and Niels Olij

FIELD OF THE INVENTION

The present invention relates to implantable medical devices and, particularly, to an implantable medical device system for locating an implantable medical device with a high degree of precision.

BACKGROUND OF THE INVENTION

Many implantable medical devices require percutaneous communication. That is, in particular regard to implantable drug infusion devices, such devices often require the drug supply to be replenished. Typically, such replenishment is accomplished by inserting a needle through the skin and into the septum of a drug reservoir in such a device.

Because such a device is implanted and thus not able to be directly seen, care must be taken to ensure that the needle is properly placed into the device before injection. If the needle misses the device and, in particular, misses the drug reservoir in the device, the drugs will be immediately dispensed in the body, having potentially dire consequences for the patient. Moreover, if the needle is not fully placed through the septum and into the drug reservoir, the drug reservoir will not be adequately filled, also having potentially dire consequences for the patient.

Previous attempts have been made to accurately locate and identify implanted devices and, in particular, septum loading to the drug reservoir of implantable drug infusion devices. For example, Celcontrol, Inc. advertised an implantable vascular access device which required the attachment of an electrode to the skin and the attachment of a wire to the hypodermic needle to create a circuit for locating the implantable device. Such a system, besides having more complexity than desired, did not provide an accurate location of the needle in relation to the device without first inserting the needle through the skin. U.S. Pat. No. 5,171,228 disclosed a further system which required an RF transmitter and a transmitting antenna. Such a system, to date, has not proven practical or provided an acceptable precision for locating the implantable device. Thus, there exists a need for a simple device and technique for sensing the position of an implanted device and, in particular, of a drug reservoir septum, without first requiring the skin to be punctured or additional electrode attachments to be made to the patient.

SUMMARY OF THE INVENTION

These and other objects are accomplished by the present invention which includes a system and method for locating an implantable medical device. The system consists of a flat "pancake" antenna coil positioned concentric with the implantable medical device target, e.g. the drug reservoir septum. The system further features a three location antenna array which is separate from the implantable device and external to the patient. The antenna array features three or more separate antennas which are used to sense the energy emitted from the implanted antenna coil. The system further features a processor to process the energy ducted by the antenna array. The system senses the proximity to the implant coil and, thus, the implant device by determining when an equal amount of energy is present in each of the antennas of the antenna array and if each such ducted energy is greater than a predetermined minimum. When such a condition is met, the antenna array is aligned with the implant coil. Thus the needle port through the antenna array is lined up with the septum of the drug reservoir. Alternative embodiments are further disclosed in which the processor and antenna array are positioned within the implanted device while the coil is external to the patient.

The FIGS. are not necessarily to scale.

DETAILED DESCRIPTION OF THE INVENTION

Figure 1:
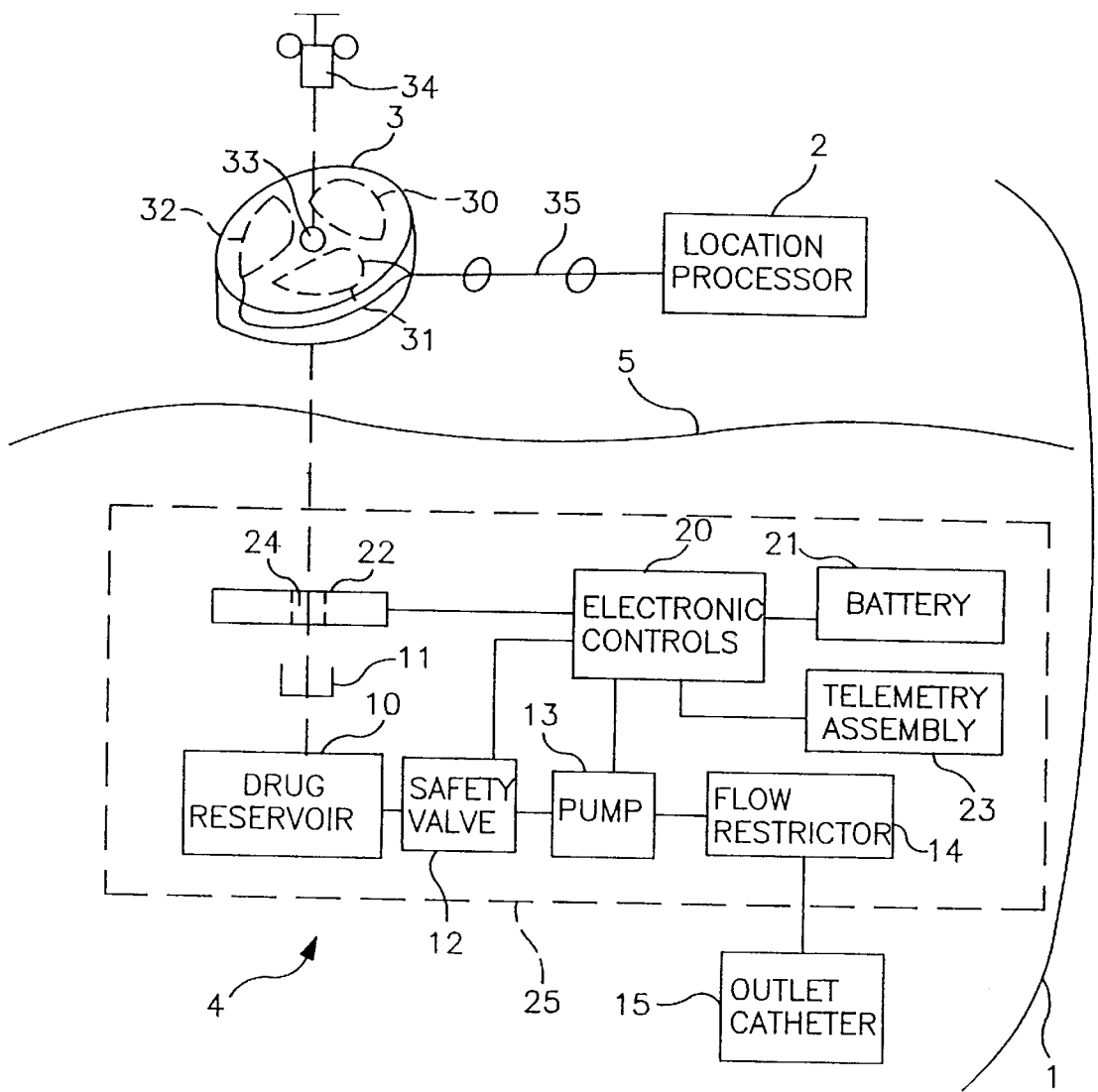
FIG. 1 is a block diagram showing the system according to the present invention.

FIG. 1 is a block diagram showing the system according to the present invention. As seen, the system 1 features a location processor 2 coupled to implant location antenna array 3 which are used to locate implantable medical device 4 positioned beneath skin of patient 5. Medical device 4 may be of any design desired, such as the Medtronic SynchroMed implantable drug pump, although other devices besides drug pumps may also be used. In the preferred embodiment device 4 includes a drug reservoir 10 having a septum 11 for drug replenishment. Drug reservoir outlets such drugs, past pump 13 to outlet catheter 15. In an additional embodiment (although illustrated here for clarity, the device could further feature a safety valve 12 and, beyond flow restrictor 14, constructed according to the above referenced U.S. patent application Ser. No.09/017,194, filed Feb. 2, 1998 entitled "Implantable Drug Infusion Device Having A Safety Valve" of Markus Haller and Koen Weijand and U.S. patent application Ser. No. 09/017,194 filed Feb. 2, 1998 entitled "Implantable Drug Infusion Device Having A Flow Regulator" of Markus Hallesr, Phillipe Renaud and Christian Amacker respectively. Electronic controls 20 powered by battery 21 provide control and energy to pump and safety valve and further to provide control and energy to implant coil 22. Device further includes a telemetry assembly 23 to provide two-way communication between device 4 and any suitable external device. As seen, implant coil 22 is positioned such that opening 24 therein is aligned with septum 11. Coil is aligned with opening centered therein. In this view implant coil is shown positioned above septum, although implant coil may also be positioned around or, indeed, beneath the septum. What is important is for coil and thus opening and septum to be aligned. As further seen, all elements of the device but the outlet catheter are housed within the hermetic enclosure 25 as is well known in the art.

As further seen in this figure, implant location antenna array 3 is movably positioned outside of patient 5. Array features three air coil antennas 30, 31 and 32 symmetrically disposed about the guide 33 and all mounted within the same plane. As seen, guide 33 is provided to permit a needle 34 to be positioned through array and thus into and past septum 11 to thereby replenish drugs in the reservoir. Each antenna is electrically coupled to location processor through a series of wires, commonly designated 35.

Figure 2A:
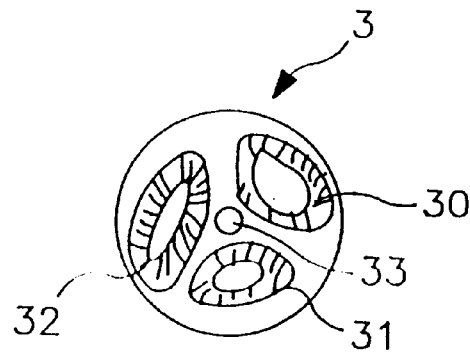
FIG. 2 is a top view of array.
Figure 2B:
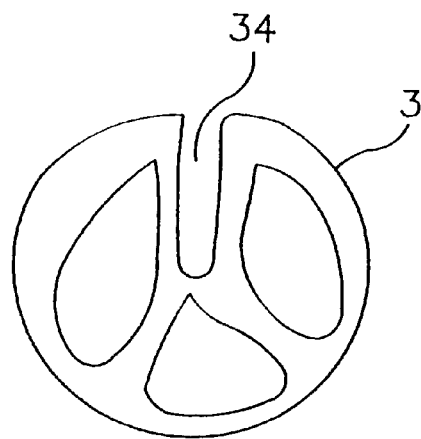

Turning now to FIG. 2 which shows a top view of array 3, as seen, antennas 30, 31 and 32 are symmetrically disposed about guide 33. Antennas, moreover, are also disposed along the same plane. Each antenna is identical, and is constructed as an planar air coil antenna, preferably from printed wiring board, although other antenna constructions may be used, such as a ferrite coil. The planar antenna is housed within a non-conductive material, such as plastic. Guide is disposed in a center location and is sized to permit a needle to be passed therethrough. Although shown as a circular passage, a needle slot 34 may further be provided, as shown in FIG. 2B. As discussed above, antenna is positioned external to the patient and is designed to be moved along the surface of the patient's body to thereby accurately locate the implant coil and thus the septum of the device.

Figure 3:
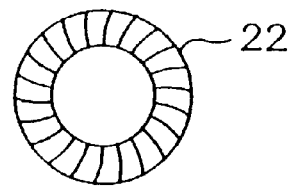
FIG. 3 is a top view of implant coil.

FIG. 3 is a top view of implant coil 22. Implant coil is constructed of any acceptable material. Although shown in FIG. 1 as a separate coil and device it should be appreciated that implant coil could also be fashioned by using an implant telemetry of the device as is well known to one skilled in the art.

Figure 4:
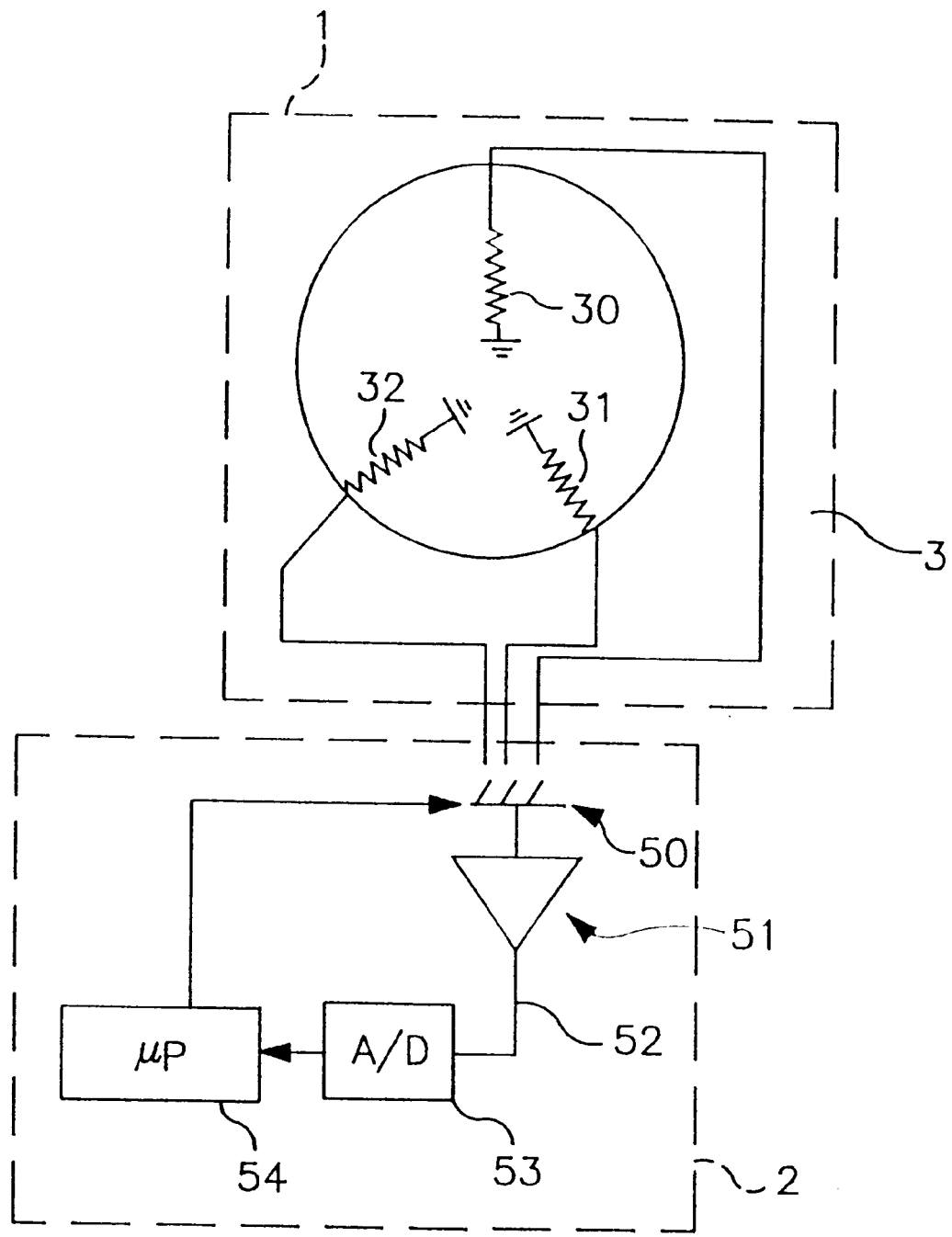
FIG. 4 discloses the circuit used in the location processor.

FIG. 4 discloses the circuit used in the location processor 2 and array 3. As seen, antennas 30, 31 and 32 disposed in array 3 are coupled into location processor 2 through switch 50. Through such a coupling this embodiment uses a sampling technique to alternatingly sample the signal on each antenna. Each such sampled signal is then passed through amplifier 51 which also provides a filtering function and outputs the signal on line 52 as an RSSI. In the preferred embodiment, amplifier is preferably NA604, available form National Semiconductor National Semiconductor Corporation, 2900 Semiconductor Drive, P.O. Box 58090, Santa Clara, Calif., 95052-8090. Signal is then processed through analog digital computer 53 where it is then put into the microprocessor 54. Microprocessor thereafter compares each of the signals sampled from the antennas and determines whether the energy received by each of the antennas is above a predetermined minimum. In such a case an operating range signal is emitted to indicate to the operator the operating distance with the implanted device, as discussed in more detail below. Microprocessor would then determine whether the same amount of energy is being sensed by each antenna, which, due to the geometry of implant coil 22 and array 3, indicates the antennas having a guide therein as well as implant coil are thus in alignment. Microprocessor would then cause to be emitted an alignment signal. As discussed in more detail below, in an alternate embodiment, rather than using a sampling technique to detect the energy sensed by each antenna, the system could also use a technique in which each coil is oppositely coupled, that is in anti-phase, such that when a null is sensed the coils are each sensing an equal amount of energy.

Figure 5:
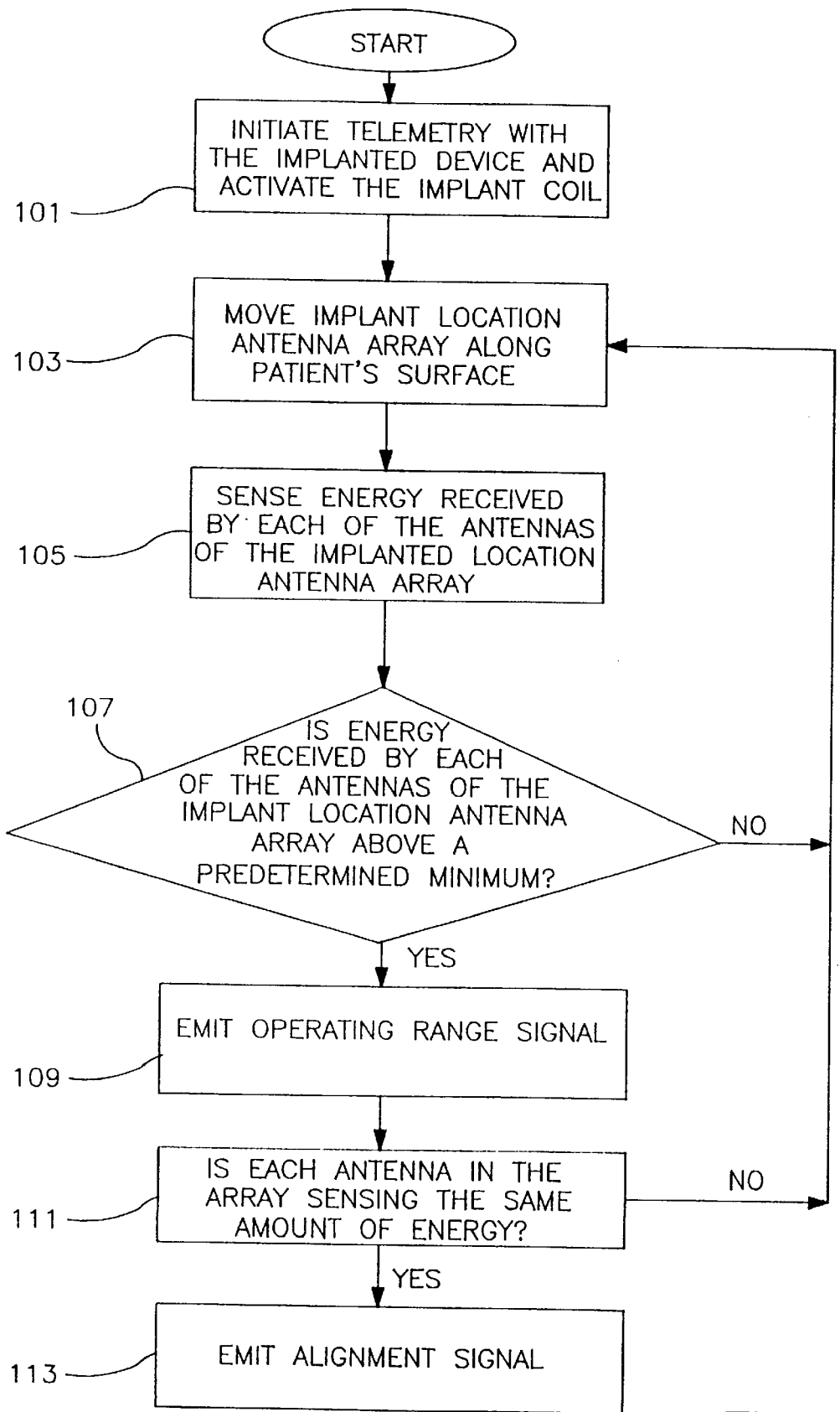
FIG. 5 discloses the procedure used to locate a device according to the present invention.

FIG. 5 discloses the procedure used to locate a device according to the present invention. As seen at 101, telemetry is initiated with the implant device. Such telemetry initiation is done to instruct the implant device to activate the implant coil. In the preferred embodiment the implant coil is activated to thereby transmit energy at a known frequency, preferably the device transmits at 32.768 kHz since this frequency is readily available in present implantable pulse generators. Next, at 103 the implant location antenna array is moved along the patient's surface. Next, at 105 the energy received by each of the antennas of the implant location antenna array is sensed. Next, at 107 device determines if such energy is above a predetermined minimum. As can be appreciated, this predetermined minimum amount of energy required to be sensed by each antenna dictates the furthest distance the antenna of the array may be from the implant coil, and still provide information regarding the location of the coil and thus the device. Although determining whether the energy sensed by each antenna is above a predetermined threshold is shown as a separate step, this could also be integrated within another step. Next, if the energy sensed is above a predetermined minimum the device goes to step 109 and emits an operating range signal, otherwise the device recycles back to step 103. Next, at 111 a comparison is made to determine if each of the antennas in the array are sensing the same amount of energy. Comparison may be made using a sampling technique, as described above in FIG. 4, or a non-sampling technique, as described below with regard to FIG. 6. With either or any other technique, if it is found each of the antennas is sensing an equal amount of energy, then If the antennas each are sensing the same amount of energy which is above the predetermined minimum, then this implies each of the antennas are positioned an equal distance away from the implant coil. Because the passage and septum are located directly centered within the array and the coil respectively, this than means that they are in alignment. Next, at 113 a signal is emitted by the location processor to indicate such alignment. The emitted signal is preferably a light, although this may also be delivered through a sound or both. In a further embodiment the array or the device may additionally feature a vibration device, which is either activated or deactivated (whichever is desired) upon alignment. Through such a manner the transmission of energy from the coil to the array may be used to precisely align the components.

Figure 6:
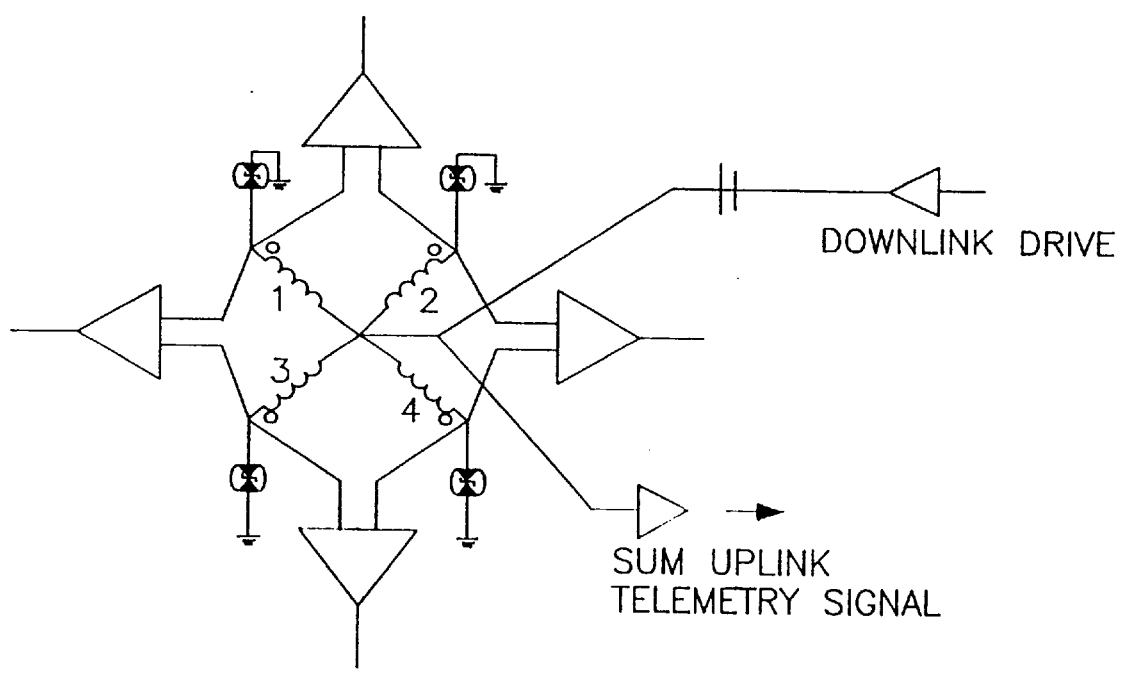
FIG. 6 discloses an alternative circuit for use in the location processor.

FIG. 6 discloses an alternative circuit for use in the location processor 2. As seen in this embodiment four separate antennas are used in the array. Each coil is further connected to the associated electronics such that the voltages from the coils are subtracted. The center connection of the coils provides the sum of the signals sensed by all the coils. Because the signal from two coils connected in antiphase is only zero, the symmetry line of these coils crosses the center of the transmitting antenna, in this case the implant coils 22. This means that all four signals derived are zero, the four symmetry lines of these antennas are crossing the center of the implant coil. In addition, the sum signal must be the maximum, or at least greater than the predetermined value, thereby indicating the antenna is in connection with an implant coil. As already discussed above, this determines that the device is within a predetermined operating range. Although shown as having four antennas, this embodiment may further be constructed using any number of antennas, from 3 to 360, for example. Among the advantages believed offered by such a configuration is the ability to combine both device telemetry and localization.

Figure 7:
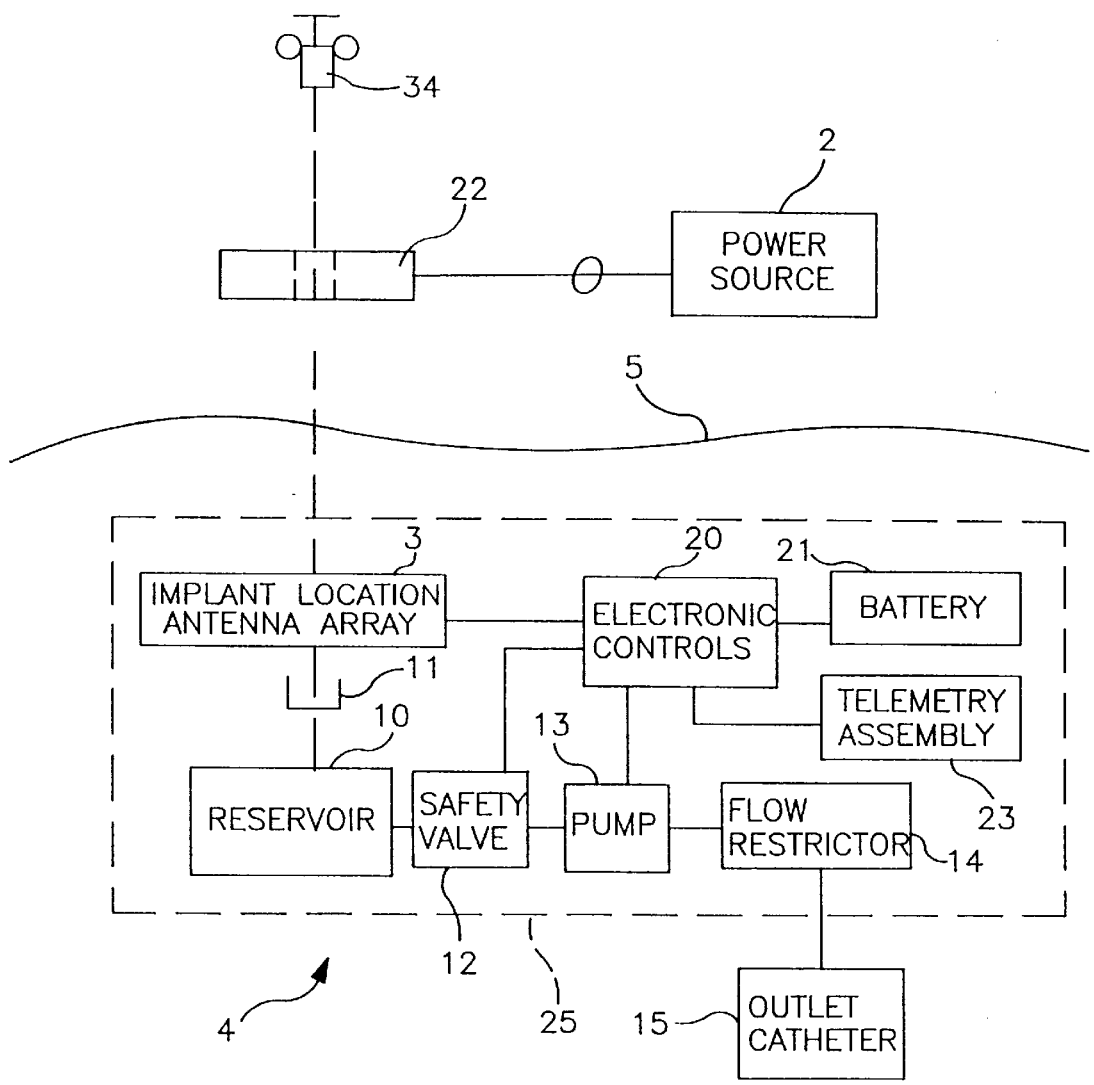
FIG. 7 is a block diagram showing an alternative system according to the present invention.

FIG. 7 is a block diagram showing an alternative system according to the present invention. As seen this system differs from that disclosed in FIG. 1 in that the location processor 2 coupled to implant location antenna array 3 are integrated within the device 4 while the coil 22 is featured outside of the patient. Like the system of FIG. 1, device 4 may still be of any design desired. Device may include a drug reservoir 10 having a septum 11 for drug replenishment. Drug reservoir outlets such drugs through safety valve 12, past pump 13, beyond flow restrictor 14 to outlet catheter 15. Electronic controls 20 powered by battery 21 provide control and energy to pump and safety valve and further to provide control and energy to implant coil 22. Device further includes a telemetry assembly 23 to provide two-way communication between device 4 and any suitable external device. In this embodiment, array 3 (rather than implant coil 22 as shown in FIG. 1) is positioned such that a guide 33 therein is aligned with septum 11. In this view array 3 is shown positioned above septum, although array 3 may also be positioned around or, indeed, beneath the septum. As already discussed above, what is important is for array 3 and in particular guide 33 and septum to be aligned, As further seen, all elements of the device but the outlet catheter are housed within the hermetic enclosure 25 as is well known in the art. As further seen, coil 22 is movably positioned outside of patient 5. Coil 22 is of the same design discussed above, and features an opening 24 (either a slot or a hole) therein to permit a needle 34 to be positioned through array and thus into and past septum 11 to thereby replenish drugs in the reservoir. In a still further embodiment a refill the syringe can be constructed having an integral coil.

Although a specific embodiment of the invention has been disclosed, this is done for purposes of illustration and is not intended to be limiting with regard to the scope of the invention. Thus the present invention as disclosed provides a method and system for accurately locating an implanted device, and in particular a septum within an implanted device, without first requiring the patient's skin to be punctured. Although the invention is described as having a separate external positioning array through which a needle is inserted, the invention may also be incorporated as a part of a needle assembly. It is contemplated various other substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A system for use in locating an implantable medical device comprising:

means for emitting a first frequency of energy, the emitting means fixed relative to a first point in space;

means for sensing the emitted energy at a first location and a second location, the first location and the second location positioned along the same plane, the sensing means fixed relative to a second point in space, the sensing means having means for moving relative to the emitting means wherein the second point in space may be moved closer to the first point in space;

means for determining whether the sensed energy at the first location equals the energy at the second location;

signal means for signaling when the sensed energy at the first location equals the energy at the second location to thereby signal the first point in space and the second point in space are aligned.

2. An implantable medical device comprising:

means for sensing energy at a at a first location and a second location, the first location and the second location fixed relative to one another along the same plane;

means for determining whether the sensed energy at the first location equals the energy at the second location.

3. A method of locating the alignment between an implanted device and an external object comprising the steps of:

emitting energy from an implanted device;

moving an implant location antenna array along a patient's surface;

sensing energy received by each of the antennas of the implant location antenna array from the implanted device;

determining whether the sensed energy received by each of the antennas of the implant location antenna array above a predetermined minimum;

determining whether the sensed energy received by each of the antennas of the implant location antenna array is at an equal level; and emitting an alignment signal when the sensed energy received by each of the antennas of the implant location antenna array is at an equal level and above the predetermined minimum.

* * * * *